(12) United States Patent
Roller et al.

(10) Patent No.: US 7,259,142 B2
(45) Date of Patent: Aug. 21, 2007

(54) REDOX-STABLE, NON-PHOSPHORYLATED CYCLIC PEPTIDE INHIBITORS OF SH2 DOMAIN BINDING TO TARGET PROTEIN, CONJUGATES THEREOF, COMPOSITIONS AND METHODS OF SYNTHESIS AND USE

(75) Inventors: Peter P Roller, Rockville, MD (US); Ya-Qui Long, Bethesda, MD (US); Feng-Di T. Lung, Taichung (TW); C. Richter King, Washington, DC (US); Dajun Yang, Gaithersburg, MD (US); Johannes H. Voigt, Cranford, NJ (US)

(73) Assignee: The United States of America, represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 11/224,819

(22) Filed: Sep. 13, 2005

(65) Prior Publication Data

US 2006/0014927 A1    Jan. 19, 2006

Related U.S. Application Data

(60) Division of application No. 09/998,350, filed on Nov. 30, 2001, now Pat. No. 6,951,915, which is a continuation-in-part of application No. PCT/US00/15201, filed on Jun. 2, 2000.

(60) Provisional application No. 60/137,187, filed on Jun. 2, 1999.

(51) Int. Cl.
*A61K 38/12*    (2006.01)

(52) U.S. Cl. .......................... 514/11; 530/317; 530/334

(58) Field of Classification Search ...................... None
See application file for complete search history.

(56) References Cited

FOREIGN PATENT DOCUMENTS

WO    WO96/23813    8/1996
WO    WO98/02176    1/1998

OTHER PUBLICATIONS

Roller, et al., Peptides 1998, Proceedings of the European Peptide Symposium, 25th , Budapest, Aug. 30-Sep. 4, 1998, 706-707.*
Jain, Science 271 :1079-1080, 1996, p. 1080.*
Dermer, Biocechonology, 1994, 12 : 320.*
Gura, Science, 1997, vol. 278, 1041.*
Landon et al., *J. Cell. Biochem.*, 90, 509-517 (2003).
Long et al. "Significant Compensatory Role of Position Y-2 Conferring High Affinity to Non-Phosphorylated Inhibitors of GRB2-SH2 Domain" *Bioorganic & Medicinal Chemistry Letters*, 9 (15), 2267-2272, (Aug. 2, 1999).
Long et al. "Structural Requirements for Tyr in the Consensus Sequence Y-E-N of a Novel Nonphosphorylated inhibitor to the Grb2-SH2 Domain" *Biochemical and Biophysical Research Communications*, 264 (3), 902-908 (1999).
Lung et al. "Novel Non-Phosphorylated Peptides Binding to the Grb2-SH2 Domain" *Proceedings of the American Peptide Symposium* (1997).
Lung et al., *Biopolymers*, 71, 132-140 (2003).
Oligino et al. "Nonphosphorylated Peptide Ligands for the Grb2 Src Homology 2 Domain" *Journal of Biological Chemistry*, 272 (46), 29046-29052, (Nov. 14, 1997).

* cited by examiner

*Primary Examiner*—Anish Gupta
*Assistant Examiner*—Satyanarayana R. Gudibande
(74) *Attorney, Agent, or Firm*—Leydig, Voit & Mayer, Ltd.

(57) ABSTRACT

A compound of formula:

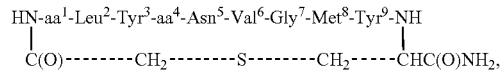

[SEQ ID NO:2]

$$\text{HN-aa}^1\text{-Leu}^2\text{-Tyr}^3\text{-aa}^4\text{-Asn}^5\text{-Val}^6\text{-Gly}^7\text{-Met}^8\text{-Tyr}^9\text{-NH}$$
$$| \qquad \qquad \qquad \qquad \qquad \qquad \qquad \qquad |$$
$$\text{C(O)--------CH}_2\text{--------S--------CH}_2\text{-----CHC(O)NH}_2,$$

in which (i) $aa^1$ is Adi and $aa^4$ is Glu or (ii) each of $aa^1$ and $aa^4$ is Adi, L is sulfur, sulfoxide, oxygen or methylene, which compound (and its conjugates) bind to an SH2 domain in a protein comprising an SH2 domain, is non-phosphorylated, is redox-stable in vivo, is characterized by an $IC_{50}$ in vivo of less than about 4.0 µM with respect to the SH2 domain in Grb2, and, upon binding to the SH2 domain of Grb2, has a turn conformation. A conjugate comprising a compound as described above and a carrier agent, a composition comprising (i) a compound or a conjugate as described above and (ii) a carrier, a method of inhibiting binding of an SH2 domain in a protein comprising an SH2 domain to a target protein in an animal, wherein the SH2 domain is contacted with a target protein-binding inhibiting effective amount of a compound or a conjugate as described above, and a method of synthesizing such conjugates.

7 Claims, No Drawings

REDOX-STABLE, NON-PHOSPHORYLATED CYCLIC PEPTIDE INHIBITORS OF SH2 DOMAIN BINDING TO TARGET PROTEIN, CONJUGATES THEREOF, COMPOSITIONS AND METHODS OF SYNTHESIS AND USE

CROSS-REFERENCE TO RELATED APPLICATIONS

This patent application is a divisional of copending U.S. patent application Ser. No. 09/998,350, filed Nov. 30, 2001, now U.S. Pat. No. 6,951,915, which is a continuation in part of International Patent Application No. PCT/US00/15201 filed Jun. 2, 2000, now WO00/73326, published Dec. 7, 2000, which claims the benefit of U.S. Provisional Patent Application No. 60/137,187 filed Jun. 2, 1999.

TECHNICAL FIELD OF THE INVENTION

The present invention relates to redox-stable, non-phosphorylated cyclic peptide inhibitors of SH2 domain binding to a target protein and conjugates of such cyclic peptide inhibitors, as well as compositions, methods of synthesis and methods of use.

BACKGROUND OF THE INVENTION

Src homology 2 (SH2) domains selectively bind to phosphotyrosyl (pTyr)-containing regions of target proteins. SH2 binding can result in the modulation of c-src activity (Cooper et al., *Cell* 73: 1051-1054 (1993)), the alteration of the substrate specificity of c-abl proto-oncoproteins (Mayer et al., *Mol. Cell. Biol.* 14: 2883-2894 (1994); Feller et al., *Trends Biochem. Sci.* 19: 453-458 (1994)) and the transduction of signals initiated at growth factor receptors (Margolis et al., *J. Am. Soc. Nephrol.* 5: 1288-1299 (1994)) and cellular attachment systems (Schlaepfer et al., *Nature* 372: 786-791 (1994)). Thus, the SH2 domain has been suggested to be a promising site for therapeutic intervention (Brugge, *Science* 260: 918-919 (1993)).

The SH2 domain of growth factor receptor-bound protein 2 (Grb2), a 24 kda intracellular carrier agent that is composed of one SH2 domain and two src homology 3 (SH3) domains, mediates cellular signaling by binding pTyr-containing motifs within several proteins, although the Grb2 SH2 domain also can bind to proteins that do not contain pTyr (Oligino et al., *J. Biol. Chem.* 272: 29046-29052 (1997)). Such proteins include the adapter protein SHC (via p52 binding; Pelicci et al., *Cell* 70: 93-104 (1992); Rozakis-Adcock et al., *Nature* 360: 689-692 (1992); Sastry et al., *Oncogene* 11: 1107-1112 (1995); Janes et al., *Oncogene* 9: 3601-3608 (1994); Daly et al., *Oncogene* 9: 2723-2727 (1994)), growth factor receptors, such as epidermal growth factor receptors (EGFR) and their oncogenic analog receptors, the erbB receptors (Rozakis-Adcock et al. (1992), supra; Lowenstein et al., *Cell* 70: 431-442 (1992); Gale et al., *Nature* 363: 88-92 (1993); Buday et al., *Cell* 73: 611-620 (1993); Egan et al., *Nature* 363: 45-51 (1993)), in particular erbB2 (HER-2 or neu; via p185 binding; Sastry et al. (1995), supra; Janes et al. (1994), supra; Daly et al. (1994), supra; Xie et al., *J. Biol. Chem.* 270: 30717-30724 (1995); Gishizky et al., *PNAS USA* 92: 10889-10893 (1995)), morphology-determining proteins, such as cytoplasmic focal adhesion protein-tyrosine kinase (FAK; Schlaepfer et al. (1994), supra), and cellular oncoproteins, such as BCR-abl (Gale et al. (1993), supra; Pendergast et al., *Cell* 75: 175-185 (1993); Xie et al. (1995), supra; Gishizky et al. (1995), supra).

The prevention of Grb2-mediated multiprotein assemblies is considered to be a promising therapeutic target for the development of antiproliferative agents directed to cells that over-express growth factor receptors. In this regard, a non-phosphorylated peptide containing 11 amino acids in which the side chains of the two terminal cysteine residues form a ring has been reported to bind selectively the SH2 domain of Grb2 (Oligino et al. (1997), supra). The cyclic structure and the size of the ring have been determined to be critical to the binding activity of the non-phosphorylated peptide, which has been designated G1. An equipotent redox-stable thioether cyclized analog, G1TE, also has been reported (Oligino et al. (1997), supra). Unfortunately, G1 and G1TE have receptor affinities that are substantially lower than a segment of the naturally phosphorylated ligand, i.e., SHC(pY$^{317}$)-9-mer (IC$_{50}$ of 10-25 µM and 10-15 µM, respectively, vs. 1.0 µM). Accordingly, the utility of G1 and G1TE in in vivo prophylactic and therapeutic applications is limited.

In view of the above, there remains a need for an effective inhibitor of binding of an SH2 domain in a protein comprising an SH2 domain to a target protein. Therefore, it is an object of the present invention to provide non-phosphorylated cyclic peptide inhibitors of SH2 domains to target proteins, such as the SH2 domain that exists in Grb2 protein, which are redox-stable in vivo and are characterized by receptor affinities that are substantially better than currently available cyclic peptide inhibitors of SH2 domains. It is another object of the present invention to provide conjugates of such cyclic peptide inhibitors in order to facilitate cellular internalization of active agents. It is yet another object of the present invention to provide a composition comprising (i) such an inhibitor or such a conjugate and (ii) a carrier. It is still yet another object of the present invention to provide a method of synthesizing such conjugates. A further object of the present invention is to provide methods of use of such inhibitors and conjugates thereof. These and other objects and advantages, as well as additional inventive features, will be apparent from the detailed description provided herein.

BRIEF SUMMARY OF THE INVENTION

The present invention provides a compound of formula:

[SEQ ID NO:1]

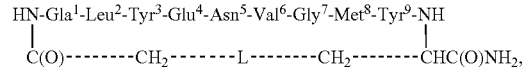

in which L is sulfur, sulfoxide, oxygen or methylene, and, optionally, one or more of Tyr$^3$, Glu$^4$, Val$^6$, Met$^8$ and Tyr$^9$ is modified. The present invention also provides a compound of formula:

[SEQ ID NO:2]

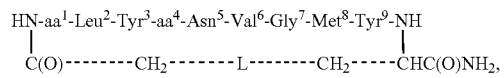

in which (i) aa$^1$ is Adi and aa$^4$ is Glu or (ii) each of aa$^1$ and aa$^4$ is Adi, and in which, L is sulfur, sulfoxide, oxygen or methylene, and, optionally, one or more of Tyr$^3$, Val$^6$, Met$^8$ and Tyr$^9$ is modified. With respect to these compounds, the modifications of the indicated amino acids desirably do not result in a highly charged moiety that prevents the compound from entering into a cell. Optionally, there is a conservative or neutral amino acid substitution at either one or both of Leu² and Gly⁷. The compounds (and their conjugates) bind an SH2 domain in a protein comprising an SH2 domain, are non-phosphorylated, are redox-stable in vivo, and are characterized by an IC$_{50}$ in vivo of less than about 4.0 μM with respect to the SH2 domain in Grb2, and, upon binding to the SH2 domain of Grb2, the compounds have a turn conformation. Preferably, the compounds (and their conjugates) have an IC$_{50}$ in vivo of less than or equal to 2.0 μM.

Also provided by the present invention is a conjugate comprising a compound as described above and a carrier agent that facilitates cellular internalization. In addition, the present invention provides a composition comprising a compound or a conjugate as described above and a carrier.

A method of inhibiting binding of an SH2 domain in a protein comprising an SH2 domain to a target protein in an animal is further provided. The method comprises contacting the SH2 domain in a protein comprising an SH2 domain with a target protein-binding inhibiting amount of a compound or a conjugate as described above, whereupon binding of the SH2 domain in the protein comprising the SH2 domain to the target protein is inhibited.

Still further provided is a method of synthesizing a conjugate described above. The method comprises:

(i) synthesizing from C-terminus to N-terminus a linear side-chain protected peptide comprising from N-terminus to C-terminus the amino acid sequence of the compound of claim 1 or 2 and the amino acid sequence of a carrier agent on an amide resin, (ii) N-terminally haloacetylating the peptide, (iii) cleaving the peptide from the resin and, either simultaneously or sequentially, deprotecting the side-chains of the peptide, (iv) nucleophilically displacing the N-terminal halo group with the cysteine side-chain thiol functionality at from about pH 7 to about pH 8, and (v) purifying the resulting conjugate.

DETAILED DESCRIPTION OF THE INVENTION

The present invention is predicated on the surprising and unexpected discovery of non-phosphorylated cyclic peptide inhibitors of binding of SH2 domains in proteins comprising SH2 domains to target proteins which not only are redox-stable in vivo but have unprecedented specific binding affinities. Previously reported non-phosphorylated cyclic peptide inhibitors of binding of SH2 domains in proteins comprising SH2 domains to target proteins had specific binding affinities that were substantially worse than the naturally occurring ligand of SH2 domains, rendering them unsuitable for in vivo applications. The discovery of such redox-stable, non-phosphorylated cyclic peptide inhibitors has involved the painstaking analysis of amino acid sequences, size constraints, the presence and absence of phosphorylation, such as that which occurs in the naturally occurring ligand of SH2 domains, cyclization linkages, modifications of amino acid side chains, affinity binding studies and molecular modeling.

In view of the above, the present invention generally provides a compound of formula:

[SEQ ID NO:3]

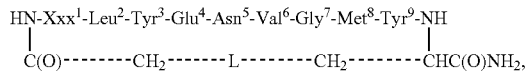

in which Xxx¹ represents a standard, naturally occurring or non-natural amino acid other than glutamic acid and L is sulfur, sulfoxide, oxygen or methylene. The side chain of Xxx¹ can be extended by one or more methylene groups provided that the compound can bind to an SH2 domain in a protein comprising an SH2 domain in accordance with the present invention. An intrachain methylene of the side chain can be substituted with O, S or N. In addition, the side chain can be terminally substituted with one or more of F and/or COOH. The other three-letter designations represent standard, naturally occurring and non-natural amino acids. The compound (and its conjugate) binds an SH2 domain in a protein comprising an SH2 domain, is non-phosphorylated, is redox-stable in vivo, and is characterized by an IC$_{50}$ in vivo of less than about 4.0 μM with respect to the SH2 domain in Grb2. Preferably, the compound (and its conjugate) has an IC$_{50}$ in vivo of less than or equal to 2.0 μM. Upon binding to the SH2 domain of Grb2, the compound has a turn conformation. Optionally, one or more of Tyr³, Glu⁴, Val⁶, Met⁸ and Tyr⁹ is modified; desirably, the modification does not result in a highly charged moiety that prevents the compound from entering into a cell. Also optionally, there is a conservative or neutral amino acid substitution at either one or both of Leu² and Gly⁷.

By "modified" is meant substitution by a naturally occurring amino acid, a D-configuration analog thereof or a non-natural amino acid. Whether or not a compound is redox-stable in vivo can be determined in accordance with methods known in the art.

Specifically, the present invention provides a compound of formula:

[SEQ ID NO:1]

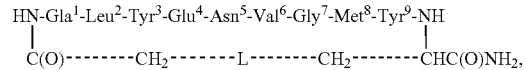

in which Gla represents γ-carboxy-L-glutamic acid or a closely related methylene $(CH_2)_x$ side chain-extended analog in which x is 2 or 3, the other three-letter designations represent standard, naturally occurring and non-natural amino acids and L is sulfur, sulfoxide, oxygen or methylene. The compound (and its conjugate) binds an SH2 domain in a protein comprising an SH2 domain, is non-phosphorylated, is redox-stable in vivo, and is characterized by an IC$_{50}$ in vivo of less than about 4.0 μM with respect to the SH2 domain in Grb2. Preferably, the compound (and its conjugate) has an IC$_{50}$ in vivo of less than or equal to 2.0 μM. Upon binding to the SH2 domain of Grb2, the compound has a turn conformation. Optionally, one or more of Tyr³, Glu⁴, Val⁶, Met⁸ and Tyr⁹ is modified; desirably, the modification does not result in a highly charged moiety that prevents the compound from entering into a cell. Also optionally, there is a conservative or neutral amino acid substitution at either one or both of Leu² and Gly⁷.

The present invention further provides a compound of formula:

[SEQ ID NO:1]

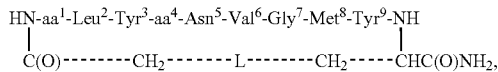

in which aa represents an amino acid as indicated, the other three-letter designations represent standard, naturally occurring and nonnatural amino acids, and L is sulfur, sulfoxide, oxygen or methylene. Accordingly, either (i) aa$^1$ is Adi and aa$^4$ is Glu or (ii) each of aa$^1$ and aa$^4$ is Adi. The compound (and its conjugate) binds an SH2 domain in a protein comprising an SH2 domain, is non-phosphorylated, is redox-stable in vivo, and is characterized by an IC$_{50}$ in vivo of less than about 4.0 µM with respect to the SH2 domain in Grb2. Preferably, the compound (and its conjugate) has an IC$_{50}$ in vivo of less than or equal to 2.0 µM. Upon binding to the SH2 domain of Grb2, the compound has a turn conformation. Optionally, one or more of Tyr$^3$, Val$^6$, Met$^8$ and Tyr$^9$ is modified; desirably, the modification does not result in a highly charged moiety that prevents said compound from entering into a cell. Also, optionally, there is a conservative or neutral amino acid substitution at either one or both of Leu$^2$ and Gly$^7$.

Such compounds can be synthesized in accordance with methods known in the art. Preferred methods are those that are set forth in the Examples, such as Examples 1, 2 and 3. The compound of Example 1 has an IC$_{50}$=0.64 µM in the Biacore binding assay described herein.

In addition to the above, the present invention provides a conjugate comprising a compound as described above and a carrier agent, which functions to internalize the compound into the cell. Examples of carrier agents include a signal peptide, antennapedia peptide, lipofectin and the like.

Such conjugates can be synthesized in accordance with methods known in the art. A preferred method is set forth in Example 12. The conjugate of Example 12 is an effective inhibitor of protein association at 2 µM concentration.

Also provided by the present invention is a method of inhibiting binding of an SH2 domain in a protein comprising an SH2 domain to a target protein in an animal. The method comprises contacting the protein comprising an SH2 domain with a target protein-binding inhibiting amount of a compound or a conjugate as described above. Upon binding of the SH2 domain by a compound or a conjugate as described above, binding of a target protein is inhibited. Preferably, the target protein is a growth factor receptor, such as an EGFR. Alternatively and also preferably, the target protein is erbB, in particular erbB-2. Other alternative and preferred embodiments of the method include ones in which the target protein is a morphology determining protein, such as FAK, a cellular attachment protein, a proto-oncoprotein, an oncoprotein, such as BCR-abl, or a mitogen-activated protein (MAP) kinase. In one application of the method, preferably inhibition of binding of a target protein by an SH2 domain in a protein comprising an SH2 domain prevents cancer, in particular breast cancer.

The method of inhibiting binding of a target protein by an SH2 domain in a protein in an animal can further comprise administering to the animal an anti-cancer agent, such as a cancer chemotherapeutic agent, such as a cytotoxic agent or its prodrug, radiation and/or a radioactive isotope. Examples of anti-cancer/cytotoxic agents and their prodrugs include genistein, okadaic acid, 1-β-D-arabinofuranosyl-cytosine, arabinofuranosyl-5-aza-cytosine, cisplatin, carboplatin, angiostatin, endostatin, anti-Her-2/neu antibody, actinomycin D, asparaginase, bis-chloro-ethyl-nitroso-urea, bleomycin, chlorambucil, cyclohexyl-chloro-ethyl-nitroso-urea, cytosine arabinoside, daunomycin, etoposide, hydroxyurea, melphalan, mercaptopurine, mitomycin C, nitrogen mustard, procarbazine, teniposide, thioguanine, thiotepa, vincristine, 5-fluorouracil, 5-fluorocytosine, adriamycin, cyclophosphamide, methotrexate, vinblastine, doxorubicin, leucovorin, taxol, anti-estrogen agents such as tamoxifen, intracellular antibodies against oncogenes, the flavonol quercetin, Guanmu-tong extract, retinoids such as fenretinide, nontoxic retinoid analogues such as N-(4-hydroxyphenyl)-retinamide (HPR), and monoterpenes such as limonene, perillyl alcohol and sobrerol. Immunomodulators and immunostimulants also can be used in the context of the present inventive methods and include, but are not limited to, various interleukins, cytokines, antibody preparations, and interferons. Desirably, inhibition of binding of a target protein by an SH2 domain in a protein comprising an SH2 domain and administration of an effective amount of an anti-cancer agent treats cancer.

In view of the above methods, the present invention further provides a composition comprising (i) a compound or a conjugate as described above and (ii) a carrier, such as a pharmaceutically acceptable carrier. Pharmaceutically acceptable carriers are well-known to those of ordinary skill in the art, as are suitable methods of administration. The choice of carrier will be determined, in part, by the particular method used to administer the composition. One skilled in the art will also appreciate that various routes of administering a composition are available, and, although more than one route can be used for administration, a particular route can provide a more immediate and more effective reaction than another route. Accordingly, there are a wide variety of suitable formulations of compositions that can be used in the present inventive methods.

A compound or conjugate thereof as described above, alone or in further combination with one or more other active agents, can be made into a formulation suitable for parenteral administration, preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multi-dose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Similarly, a formulation suitable for oral administration can include lozenge forms, which can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

An aerosol formulation suitable for administration via inhalation also can be made. The aerosol formulation can be placed into a pressurized acceptable propellant, such as dichlorodifluoromethane, propane, nitrogen, and the like.

A formulation suitable for topical application can be in the form of creams, ointments, or lotions.

A formulation for rectal administration can be presented as a suppository with a suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate.

The dose administered to an animal, such as a mammal, particularly a human, in the context of the present invention should be sufficient to effect a prophylactic or therapeutic response as desired in the animal over a reasonable time frame. The dose will be determined by the potency of the particular compound or conjugate as described above, the severity of a condition being treated, such as cancer, as well as the body weight and age of the animal. The size of the dose also will be determined by the existence of any adverse side effects that may accompany the use of the particular compound or conjugate. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a compound or conjugate, alone or in combination with other active agents, such as anticancer agents, calculated in an amount sufficient to produce the desired effect in association with a pharmaceutically acceptable diluent, carrier, or vehicle. The specifications for the unit dosage forms of the present invention depend on the particular embodiment employed and the effect to be achieved, as well as the pharmacodynamics associated with each compound or conjugate in the host animal. The dose administered should be, with respect to a present inventive compound or conjugate as set forth above, a "target protein binding-inhibiting amount" or, with respect to an anti-cancer agent, an "effective amount" or an amount necessary to achieve an "effective level" in the animal. The "effective level" is used as the preferred endpoint for dosing, the actual dose and schedule can vary, depending on interindividual differences in pharmacokinetics, drug distribution, and metabolism.

One skilled in the art can easily determine the appropriate dose, schedule, and method of administration for the exact formulation of the composition being used, in order to achieve the desired "effective level" in the individual patient. One skilled in the art also can readily determine and use an appropriate indicator of the "effective level" of the compounds of the present invention by a direct (e.g., tumor biopsy or radio-imaging of the tumor) or indirect (e.g., PSA levels in the blood) analysis of appropriate patient samples (e.g., blood and/or tissues).

A method of synthesizing a conjugate described above is also provided. The method comprises:

(i) synthesizing from C-terminus to N-terminus a linear side-chain protected peptide comprising from N-terminus to C-terminus the amino acid sequence of the compound of claim 1 or 2 and the amino acid sequence of a carrier agent on an amide resin, (ii) N-terminally haloacetylating the peptide, (iii) cleaving the peptide from the resin and, either simultaneously or sequentially, deprotecting the side-chains of the peptide, (iv) nucleophilically displacing the N-terminal halo group with the cysteine side-chain thiol functionality at from about pH 7 to about pH 8, and (v) purifying the resulting conjugate.

Preferably, the haloacetylating is bromoacetylating or chloroacetylating.

The method is exemplified herein in Example 12. Suitable side-chain protections are listed under "EXAMPLES" herein. The resulting conjugate can be purified by any suitable means, such as reverse-phase HPLC.

EXAMPLES

The following examples serve to illustrate the present invention and are not intended to limit the scope of the present invention in any way. The PAL amide resin and fluorenylmethoxycarbonyl (Fmoc) derivatives of standard amino acids were obtained from Perkin-Elmer/Applied Biosystems Division (Foster City, Calif.). Side-chain protections were as follows: Glu(t-Bu), Tyr(t-Bu), Asn(Trt), and Cys(Trt). Fmoc-γ-carboxy-L-Glu(OtBu)$_2$—OH [Fmoc-Gla(OtBu)$_2$OH], Fmoc-L-α-aminoadipic acid-δ-t-butyl ester [Fmoc-Adi(OtBu)OH] and Fmoc-L-tyrosine(O-malonyl-di-OtBu)-OH [Fmoc-Tyr(O-malonyl-di-OtBu)OH] were purchased from BACHEM (Torrance, Calif.). Trifluoroacetic acid (TFA), triethylsilane (TES) and chloroacetic acid were purchased from Fluka (Ronkonkoma, N.Y.). O-benzotriazol-1-yl-N,N,N$^1$,N$^1$-tetramethyluronium hexafluorophosphate/1-hydroxybenzotriazole (HBTU/HOBt) activation of N$^α$-protected amino acids was employed for coupling and 20% piperidine/dimethylformamide (DMF) was used for Fmoc deprotection. O-(7-azabenzotriazol-1-yl)-N,N,N$^1$,N$^1$-tetramethyluronium hexafluorophosphate/1-hydroxy-7-azabenzotriazole/diisopropylethylamine (HATU/HOAt/DIEA) in DMF was used for backbone cyclization; 7-azabenzotriazole-1-yl-oxy-tris(pyrrolidino)phosphonium-hexafluorophosphate (PyAOP; available from Perspective Biosystems, Inc., Framington, Mass.)/HOAt/DIEA in DMF was used for backbone cyclization of Adi-containing compounds. TFA/TES/H$_2$O (9.5:0.25:0.25) was used for the resin cleavage and side-chain deblocking. The crude peptides were purified to homogeneity by reverse-phase high-performance liquid chromatography (RP-HPLC). HPLC conditions: Vydac C$_{18}$ column (10×250 mm); solvent gradient, A, 0.05% TFA in water; B, 0.05% TFA in 90% acetonitrile in water with gradient indicated below; flow rate, 2.5 ml/min; UV detector, 225 nm. Fast atom bombardment mass spectrometry (unit resolution, glycerol matrix) was performed on a VG Analytical 7070E-HF mass spectrometer. The purity of products was characterized by analytical HPLC and thin layer chromatography (TLC). Amino acid analysis (6 N HCl, 110° C., 24 h) was carried out at the Protein Structure Laboratory (University of California, Davis, Calif.).

Example 1

This example describes the synthesis of cyclo($CH_2$CO-Gla$^1$-Leu$^2$-Tyr$^3$-Glu$^4$-Asn$^5$-Val$^6$-Gly$^7$-Met$^8$-Tyr$^9$-Cys)-amide [SEQ ID NO: 4; in SEQ ID NO: 1, L=S].

Using an ABI 433A peptide synthesizer and FastMoc chemistry (Field et al., Pep. Res. 4: 95 (1991)), the linear side-chain protected peptide Gla-LYENVGMYC [SEQ ID NO: 5] was synthesized on the PAL amide resin (0.189 g, 0.1 mmol, 0.53 mmol/g) coupled with the respective amino acids and the N$^α$-Fmoc group of the resin-bound protected peptide was removed with 20% piperidine/DMF (12 min). After cycles of deprotection and coupling, $NH_2$-Gla(OtBu)$_2$-Leu-Tyr(tBu)-Glu(OtBu)-Asn(Trt)-Val-Gly-Met-Tyr(tBu)-Cys(Trt)-C(O)NH-Resin [SEQ ID NO: 6] was obtained. The resin-bound protected peptide was N-terminally chloroacetylated with (ClCH$_2$CO)$_2$O. For this purpose, (ClCH$_2$CO)$_2$O was prepared by mixing 0.5 M ClCH$_2$COOH/DCM (48 mg, 0.5 mmol, 1.0 ml) and 0.5 M DCC/DCM (52 mg, 0.25 mmol, 0.5 ml) for 0.5 h at RT. The precipitated dicyclohexylurea (DCU) was filtered off and the filtrate was added to the peptide resin. The resulting reaction mixture was shaken at RT for 6 h; Ninhydrin test was negative. The peptide ClCH$_2$C(O)—NH-Gla-Leu-Tyr-Glu-Asn-Val-Gly-Met-Tyr-C(CH$_2$SH)C(O)NH$_2$ [SEQ ID NO: 7] was cleaved from the resin using TFA containing 2.5% each (v/v) of TES and deionized H$_2$O (2 h). Two-thirds of the cleavage reagent mixture was evaporated under N$_2$ and the mixture was triturated in ice-cold ether to isolate the product. The precipitated crude peptide, ClCH$_2$CO-Gla-Leu-Tyr-Glu-Asn-Val-Gly-Met-Tyr-Cys-amide [SEQ ID NO: 7], was dissolved in 50 ml water, and added dropwise into 100 ml of H$_2$O solution, which was adjusted to pH 8-9 with triethylamine, repeatedly. Under basic conditions, the N-chloroacetylated linear peptide spontaneously cyclized by intramolecular nucleophilic displacement of the chloro group by cysteine thiol. Cyclization was monitored by HPLC. After 6-7 h at RT, the solution was acidified with 30% AcOH aqueous solution and lyophilized. The product was purified by RP-HPLC (gradient 20-70% B over 27 min, $R_t$=11.4 min) to provide cyclo(CH$_2$CO-Gla$^1$-Leu$^2$-Tyr$^3$-Glu$^4$-Asn$^5$-Val$^6$-Gly$^7$-Met$^8$-Tyr$^9$-Cys)-amide [SEQ ID NO: 4] in 30% yield. FAB-MS (M+H)$^+$1303.4 (calc'd 1303.5). Amino acid analysis: Asp+S-CM-Cys 1.51 (1 each), Val 1.00 (1), Leu 1.23 (1), Glu+Gla 1.88 (1 each), Gly 1.18 (1), Tyr 1.83 (2), Met 0.85 (1).

Example 2

This example describes the synthesis of cyclo(CH$_2$CO-Adi$^1$-Leu$^2$-Tyr$^3$-Glu$^4$-Asn$^5$-Val$^6$-Gly$^7$-Met$^8$-Tyr$^9$-Cys)-amide [SEQ ID NO: 8].

Cyclo(CH$_2$CO-Adi$^1$-Leu$^2$-Tyr$^3$-Glu$^4$-Asn$^5$-Val$^6$-Gly$^7$-Met$^8$-Tyr$^9$-Cys)-amide [SEQ ID NO: 8] was prepared analogously to cyclo(CH$_2$CO-Gla$^1$-Leu$^2$-Tyr$^3$-Glu$^4$-Asn$^5$-Val$^6$-Gly$^7$-Met$^8$-Tyr$^9$-Cys)-amide [SEQ ID NO: 4] as described in Example 1. Product characterization: RP-HPLC $R_t$=13.6 min (gradient 20-70% B over 27 min) in overall yield of 40%. FAB-MS (M+H)$^+$1273.4 (calc'd 1273.5). Amino acid analysis: Asp 0.43 (1), S-CM-Cys 0.98 (1), Adi 0.97 (1), Val 1.00 (1), Leu 1.21 (1), Glu 1.09 (1), Gly 1.13 (1), Tyr 1.87 (2), Met 0.93 (1).

Example 3

This example describes the synthesis of cyclo(CH$_2$CO-Adi$^1$-Leu$^2$-Tyr$^3$-Adi$^4$-Asn$^5$-Val$^6$-Gly$^7$-Met$^8$-Tyr$^9$-Cys)-amide [SEQ ID NO: 9].

Cyclo(CH$_2$CO-Adi$^1$-Leu$^2$-Tyr$^3$-Adi$^4$-Asn$^5$-Val$^6$-Gly$^7$-Met$^8$-Tyr$^9$-Cys)-amide [SEQ ID NO: 9] was prepared analogously to cyclo(CH$_2$CO-Gla$^1$-Leu$^2$-Tyr$^3$-Glu$^4$-Asn$^5$-Val$^6$-Gly$^7$-Met$^8$-Tyr$^9$-Cys)-amide [SEQ ID NO: 4] as described in Example 1. Product characterization: RP-HPLC $R_t$=13.8 min (gradient 20-70% B over 27 min). FAB-MS (M+H)$^+$ 1287.2 (calc'd 1287.5).

Example 4

This example describes the synthesis of an L=sulfoxide linkage in a compound of any of Examples 1-3, in which the Met$^8$ is simultaneously substituted by the oxidation-stable norleucine (Nle) amino acid. For purposes of illustration, the synthesis of cyclo(CH$_2$CO-Glu$^1$-Leu$^2$-Tyr$^3$-Glu$^4$-Asn$^5$-Val$^6$-Gly$^7$-Nle$^8$-Tyr$^9$-Cys)-amide-sulfoxide [SEQ ID NO: 10] is described.

Thus, for example, the resin-bound, protected peptide NH$_2$-Glu(OtBu)-Leu-Tyr(OtBu)-Glu(OtBu)-Asn(Trt)-Val-Gly-Met-Tyr(OtBu)-Nle-C(O)NH-resin [SEQ ID NO: 11] was synthesized using FastMoc chemistry. This resin-bound peptide was N-terminally chloroacetylated, cleaved from the resin, side-chain deprotected and thioether cyclized according to the above-described procedures to produce cyclo (CH$_2$CO-Glu$^1$-Leu$^2$-Tyr$^3$-Glu$^4$-Asn$^5$-Val$^6$-Gly$^7$-Nle$^8$-Tyr$^9$-Cys)-amide [SEQ ID NO: 12]. The resulting thioether was oxidized by 5% H$_2$O$_2$ aqueous solution (1 mg/ml) with stirring at room temperature for 6 hr. The oxidation process was monitored by HPLC. After lyophilizing, the crude product was purified by RP-HPLC and two diastereoisomers were obtained with Rt of 13.0 min and 14.2 min (gradient 25-40% B over 30 min). The faster-eluting fraction: FAB-MS (M+H)$^+$1258.1 (calcd 1257.5). Amino acid analysis: Asp 0.90 (1), Val 1.03 (1), Leu 1.09 (2), Glu 1.79 (2), Gly 0.93 (1), Tyr 1.12 (2)*, Nle 1.04 (1). The slower-eluting fraction: FAB-MS (M+H)$^+$1258.1 (calcd 1257.5). Amino acid analysis: Asp 0.79 (1), Val 1.03 (1), Leu 1.12 (1), Glu 1.64 (2), Gly 1.01 (1), Tyr (0.85) (2)*, Nle 1.08 (1).

Example 5

This example describes the synthesis of an L=methylene linkage in a compound of any of Examples 1-3. For purposes of illustrate, the synthesis of cyclo(Glu$^1$-Leu$^2$-Tyr$^3$-Glu$^4$-Asn$^5$-Val$^6$-Gly$^7$-Nle$^8$-Tyr$^9$-[L-α-aminoadipate])-amide [SEQ ID NO: 13] is described. (NOTE: In this structure, the side-chain carboxyl of α-aminoadipic acid was cyclized by forming an amide bond with the N-terminal amino functionality of Glu$^1$. Also, the unnatural amino acid N$^α$-Fmoc-L-α-aminoadipic acid-δ-allyl ester was incorporated onto the synthesis resin as the first amino acid.)

The linear peptide NH$_2$-Glu(OtBu)-Leu-Tyr(OtBu)-Glu(OtBu)-Asn(Trt)-Val-Gly-Met-Tyr(OtBu)-Adi(OAl)-NH-resin [SEQ ID NO: 14] was assembled by standard solid phase methods (using the ABI 433A Peptide Synthesizer and FastMoc chemistry). Next, the allyl group was removed from the Adi sidechain. Accordingly, 0.292 g of the peptide resin (0.083 mmol) was suspended on 10 ml of DMF-THF-0.5 M HCl-morpholine (2:2:1:0.1 v/v) and treated with Pd(PPh$_3$)$_4$ (0.593 g, 0.513 mmol) for 2.5 hr under N$_2$. The resin was then washed with THF (3×2 min), DMF (3×2 min), DCM (3×2 min), DIEA-DCM (1:19) (3×2 min), DCM (3×2 min), sodium diethyldithiocarbamate-DMF (5 g/l; 3×15 min), DMF (5×2 min), and DCM (3×2 min). The head-to-tail side-chain cyclization of the resin-bound peptide was performed with PyAOP (458 mg, 0.88 mmol), HOAt (120 mg, 0.88 mmol), and DIEA (306 ml, 1.76 mmol) in dry DMF at room temperature overnight. After resin cleavage and side-chain deprotection with TFA-TES-H$_2$O (9.5:0.25:0.25, v/v), the crude peptide was purified by RF-HPLC, R$_t$=13.5 min (gradient 20-70% B over 30 min). FAB-MS (M+H)$^+$1241.2 (calcd 1241.5).

Example 6

This example describes a potential method of synthesis of an L=oxygen linkage in a compound of any of Examples 1-3.

An ether-cyclized compound of any of Examples 1-3 is prepared in accordance with the method of Example 5, except that the N$^\alpha$-Fmoc-L-α-aminoadipic acid-δ-allyl ester is replaced with N$^\alpha$-Fmoc-L-(O-carboxymethyl-allyl ester)-serine.

Example 7

This example describes the affinity characteristics of the present inventive compounds for binding to the SH2 domain of Grb2.

The competitive binding affinity of the present inventive compounds was assessed using Biacore Surface Plasmon Resonance (SPR) methods utilizing a Biacore 2000 instrument. The concentrations at which half-maximal competition was observed (IC$_{50}$) were determined by mixing the inhibitor with recombinant GST-Grb2 SH2 protein and measuring the amount of competitive binding at equilibrium to an immobilized (via biotin conjugation to streptavidin coated surface of the Biacore sensor chip SA; 2 nM concentration) SHC(pTyr-317)-9-mer phosphopeptide in a manner similar to that reported previously (Oligino et al. (1997), supra). Specifically, competitive binding assays were carried out at 5 μl/min flow rate, with GST-Grb2-SH2 (150-250 nM) and a cyclic peptide inhibitor (10 nM-2 mM) in phosphate-buffered saline (PBS), pH 7.4, containing 0.01% P-20 surfactant (Biacore, Inc., Piscataway, N.J.) for a total of 10 min. The change in response units (RU) at equilibrium was measured from the absorption profiles and the percent of control (no added peptide) was calculated. The IC$_{50}$ for cyclo(CH$_2$CO-Adi$^1$-Leu$^2$-Tyr$^3$-Glu$^4$-Asn$^5$-Val$^6$-Gly$^7$-Met$^8$-Tyr$^9$-Cys)-amide [SEQ ID NO: 8] was 3.45±0.15 μM, whereas the IC$_{50}$'s for cyclo(CH$_2$CO-Adi$^1$-Leu$^2$-Tyr$^3$-Adi$^4$-Asn$^5$-Val$^6$-Gly$^7$-Met$^8$-Tyr$^9$-Cys)-amide [SEQ ID NO: 9] and cyclo(CH$_2$CO-Gla$^1$-Leu$^2$-Tyr$^3$-Glu$^4$-Asn$^5$-Val$^6$-Gly$^7$-Met$^8$-Tyr$^9$-Cys)-amide [SEQ ID NO: 4] were 3.05±0.05 μM and 0.64±0.10 μM, respectively. The results represent the mean value of at least two independent experiments.

Example 8

This example describes the ability of the present inventive compounds to inhibit growth factor receptor (p185$^{erbB-2}$) interaction with Grb2 in cell homogenates.

Cell lysates were prepared from the serum-treated erbB-2-overexpressing breast cancer cell line MDA-MB-453 using 1% Triton X-100 in PBS containing 0.2 mM NaVO$_4$. Lysates were incubated with the present inventive cyclic peptide inhibitors specified in Example 1 and Example 12, at concentrations of 0.1, 0.4, 2, 10 and 50 μM. No inhibitor was used as a control. Cell lysates were prepared using 1% Triton X-100 in PBS containing 0.2 mM NaVO$_4$. Grb2 and associated Grb2-binding proteins were immunoprecipitated from each lysate (500 μg) with anti-Grb2 antibodies and collected using protein A Sepharose using methods previously described. Immunoprecipitated proteins were separated by SDS-PAGE on 8-16% gradient gels (Novex). pTyr-containing proteins were detected by Western blotting using anti-phosphotyrosine antibodies (Upstate Biotechnology Inc.). Previous experiments have shown that a major tyrosine phosphorylated protein in MDA-MB-453 cells is p185$^{erbB-2}$, which is overexpressed as a consequence of gene amplification. The same membrane was then re-probed with anti-Grb2 antibody for Western blotting to demonstrate equal loading. A dose-dependent inhibition of the p185$^{erbB-2}$ receptor association with the Grb2 adapter protein was observed. A half-maximal inhibition of this protein association was observed at 2 μM with the inhibitors of Examples 1 and 12.

Example 9

This example describes the ability of the present inventive compounds to inhibit intracellular protein-protein interaction between p185$^{erbB-2}$ and Grb2.

The compound of Example 1, and the conjugate of Example 12, were tested in MDA-MB-453 cells (breast cancer cells that overexpress p185$^{erbB-2}$ receptor) at inhibitor concentrations of 0.1, 0.4, 2, 10 and 50 μM. In the control experiment, no inhibitor was used. The cells were treated for 3 hrs in serum-free IMEM medium. The cells were washed twice with ice-cold PBS to remove the residual inhibitory compound that was not internalized.

Cell lysates were prepared using 1% Triton X-100 in PBS containing 0.2 mM NaVO$_4$. Grb2 and associated Grb2-binding proteins were immunoprecipitated from each lysate (500 μg) with anti-Grb2 antibodies and collected using protein A Sepharose using methods previously described. Immunoprecipitated proteins were separated by SDS-PAGE on 8-16% gradient gels (Novex). pTyr-containing proteins were detected by Western blotting using anti-phosphotyrosine antibodies (Upstate Biotechnology Inc.). Previous experiments have shown that a major tyrosine phosphorylated protein in MDA-MB-453 cells is p185$^{erbB-2}$, which is overexpressed as a consequence of gene amplification. The same membrane was then re-probed with anti-Grb2 antibody for Western blotting to demonstrate equal loading.

In these whole cell assays the agents were applied to the cell culture media of MDA-MB-453 cells. These conditions required that compounds transit through the cell membrane. A clear dose-dependent reduction in the associated p185$^{erbB-2}$ bound to Grb2 was found in the cells when cells were pre-treated with increasing amounts of the peptide conjugated to carrier (Example 12). This carrier-conjugated peptide effectively inhibited the protein association at 2 μM. Moreover, the peptide (Example 1) that was not conjugated to a carrier also showed effective inhibition of p185$^{erbB-2}$/Grb2 association in cells at 50 μM concentration, indicating an ability to cross the cell membrane.

Example 10

This example describes the ability of the present inventive compounds to inhibit MAP kinase activation.

Serum-starved SAA cells are treated with a compound of any of Examples 1-3 and EGF. Cells are washed and lysed and a fraction of cell lysate is immunoprecipitated with a polyclonal anti-ERK2 antibody (Santa Cruz). The complexes on protein A Sepharose beads are washed and incubated with 10 μCi of γ-$^{32}$P-ATP (ICN Biochemicals, Cleveland, Ohio) and 0.25 mg/ml of myelin basic protein (Sigma) in 50 mM HEPES (pH 7.2), 10 mM magnesium acetate, 1 mM dithiothreitol, and 20 mM ATP at 30° C. for 20 min. The kinase reaction is quenched with sample buffer. The samples are separated on 15% SDS-PAGE, transferred to nitrocellulose and subjected to autoradiography.

Example 11

This example describes the application of molecular modeling for predicting the binding mode of the present inventive compounds to the SH2 domain of Grb2.

Molecular modeling simulations were performed with the Insight II 97/Discover 3.0 modeling package from Molecular Simulations, Inc., San Diego, Calif., with the cff91-force field. The X-ray structure of the KPFpYVNV [SEQ ID NO: 15] peptide ligand bound to the Grb2-SH2 was used as a starting geometry (Rahuel et al., *Nature Struct. Biology* 3: 586 (1996)). The positions of the backbone atoms and the side-chain atoms of those residues in the turn region (FpYVNV [SEQ ID NO: 16]) of the reference peptide sequence were used as the initial atom positions of the sub-sequence LYENV [SEQ ID NO: 17], since a turn structure has been predicted for this sub-sequence also. Then, the remaining residues of a compound in accordance with the present invention were added to the model. The —CO(Y), E, N and NH(V)-atoms, which comprise the turn, and the protein atoms were kept fixed during the following minimization and 50 simulated annealing (SA) situation. In each SA run, a different random seed was used. The same minimized starting geometry was subjected to a molecular dynamics simulation at 2,000 K for 10 ps and consecutively cooled in 5 K increments to 5 K during 195 ps. The final structure with the lowest energy was taken.

Adi$^1$ or Gla$^1$ remarkably improved the binding efficacy over Glu$^1$ by 6-fold and 31-fold, respectively. The side chains of Adi$^1$ and Gla$^1$ are believed to have similar and overlapping roles with the phosphorylated Tyr$^3$ in the naturally occurring ligand. Based on such results, it is believed that amino acids in the first position of the compound that possess flexible alkyl chains can orient the polar carboxyl groups to an optimal position for bonding interactions with the SH2 domain of a target protein.

Docking of cyclo(CH$_2$CO-Gla$^1$-Leu$^2$-Tyr$^3$-Glu$^4$-Asn$^5$-Val$^6$-Gly$^7$-Met$^8$-Tyr$^9$-Cys)-amide [SEQ ID NO: 4] into the Grb2-SH2 binding pocket, assuming that Tyr$^3$ and Asn$^5$ occupy near proximal binding sites before dynamic simulation, indicates that Gla$^1$ is favored over Glu$^1$ because the second carboxyl group of the side-chain can undergo additional interactions within the binding pocket of pTyr than the naturally occurring ligand. The resulting modified carboxyl side-chain(s) provide for more favorable ionic interactions with the guanidino functionalities of Arg 67 and Arg 86 in Grb2.

Example 12

This example describes the synthesis and characterization of an active peptide with high affinity for Grb2 conjugated to a signal peptide as a carrier agent.

Using an ABI 433A peptide synthesizer and FastMoc chemistry, the linear side-chain protected peptide, Gla$^1$-Leu$^2$-Tyr$^3$-Glu$^4$-Asn$^5$-Val$^6$-Gly$^7$-Met$^8$-Tyr$^9$-Cys-Ala-Ala-Val-Ala-Leu-Leu-Pro-Ala-Val-Leu-Leu-Ala-Leu-Leu-Ala-Pro [SEQ ID NO: 18], was synthesized on a PAL amide resin, which comprises the signal peptide (in italics) of the Kaposi fibroblast growth factor (Rojas et al., *J. Biol. Chem.* 271: 27456-27461 (1996)). The resin-bound peptide was N-terminally chloroacetylated, cleaved from the resin and side-chain deprotected, using similar conditions to those described in Example 1. Cyclization was achieved by nucleophilic displacement of the N-terminal chloride with the cysteine side-chain thiol functionality at pH 8 over a period of 6 hours. The resulting peptide cyclo(CH$_2$CO-Gla$^1$-Leu$^2$-Tyr$^3$-Glu$^4$-Asn$^5$-Val$^6$-Gly$^7$-Met$^8$-Tyr$^9$-Cys)-NH-Ala-Ala-Val-Ala-Leu-Leu-Pro-Ala-Val-Leu-Leu-Ala-Leu-Leu-Ala-Pro [SEQ ID NO: 19] was purified by RP-HPLC. HPLC conditions: Vydac C4 column (20×250 mm), flow rate 10 ml/min, solvent A, 0.05% TFA in water; B, 0.05% TFA in 90% acetonitrile in water; UV detector, 225 nm; gradient 40-90% B over 27 in; Rt=20.6 min. FAB-MS (M+Na)$^+$ 2823.4 (calc'd 2824.3).

The references, including journal articles, patent applications and patents, cited herein are hereby incorporated in their entireties by reference.

While this invention has been described with an emphasis upon preferred embodiments, it will be obvious to those of ordinary skill in the art that variations of the preferred compounds, conjugates, compositions and methods may be used and that it is intended that the invention may be practiced otherwise than as specifically described herein. Accordingly, this invention includes all modifications encompassed within the spirit and scope of the invention as defined by the following claims.

SEQUENCE LISTING

```
<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Gla, which is gamma-carboxy-L-glutamic
      acid
<220> FEATURE:
<221> NAME/KEY: misc_feature
```

```
<222> LOCATION: (1)..(9)
<223> OTHER INFORMATION: Xaa (Gla) and Tyr at position 9 are bridged
      together, making this peptide cyclic
<220> FEATURE:
<221> NAME/KEY: misc_feature
<222> LOCATION: (9)..(9)
<223> OTHER INFORMATION: Tyr at position 9 is an amide, i.e. C(O)NH

<400> SEQUENCE: 1

Xaa Leu Tyr Glu Asn Val Gly Met Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa at position 1 is alpha-amino-adipic acid
      (Adi)
<220> FEATURE:
<221> NAME/KEY: misc_feature
<222> LOCATION: (1)..(9)
<223> OTHER INFORMATION: Xaa at position 1 and Tyr at position 9 are
      bridged together, making this peptide cyclic
<220> FEATURE:
<221> NAME/KEY: misc_feature
<222> LOCATION: (4)..(4)
<223> OTHER INFORMATION: Xaa at position 4 is Glu or Adi
<220> FEATURE:
<221> NAME/KEY: misc_feature
<222> LOCATION: (9)..(9)
<223> OTHER INFORMATION: Tyr at position 9 is an amide, i.e., C(O)NH

<400> SEQUENCE: 2

Xaa Leu Tyr Xaa Asn Val Gly Met Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is any amino acid other than Glu
<220> FEATURE:
<221> NAME/KEY: misc_feature
<222> LOCATION: (1)..(9)
<223> OTHER INFORMATION: Xaa and Tyr at position 9 are bridged together,
      making this peptide cyclic
<220> FEATURE:
<221> NAME/KEY: misc_feature
<222> LOCATION: (9)..(9)
<223> OTHER INFORMATION: Tyr at position 9 is an amide, i.e., C(O)NH

<400> SEQUENCE: 3

Xaa Leu Tyr Glu Asn Val Gly Met Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: Xaa = Gla, which is gamma-carboxy-L-glutamic
      acid
<220> FEATURE:
<221> NAME/KEY: misc_feature
<222> LOCATION: (1)..(10)
<223> OTHER INFORMATION: Xaa (Gla) and Cys are bridged together, making
      this peptide cyclic
<220> FEATURE:
<221> NAME/KEY: misc_feature
<222> LOCATION: (10)..(10)
<223> OTHER INFORMATION: Cys at position 10 is an amide, i.e., C(O)NH

<400> SEQUENCE: 4

Xaa Leu Tyr Glu Asn Val Gly Met Tyr Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Gla, which is gamma-carboxy-L-glutamic
      acid

<400> SEQUENCE: 5

Xaa Leu Tyr Glu Asn Val Gly Met Tyr Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Gla(OtBu)2, which is di-
      tert-butoxy-gamma-carboxy-L-glutamic acid
<220> FEATURE:
<221> NAME/KEY: misc_feature
<222> LOCATION: (3)..(3)
<223> OTHER INFORMATION: Tyr at position 3 is modified to Tyr(tBu),
      which is tert-butyl-tyrosine
<220> FEATURE:
<221> NAME/KEY: misc_feature
<222> LOCATION: (4)..(4)
<223> OTHER INFORMATION: Glu at position 4 is modified to Glu(OtBu),
      which is tert-butoxy-glutamic acid
<220> FEATURE:
<221> NAME/KEY: misc_feature
<222> LOCATION: (5)..(5)
<223> OTHER INFORMATION: Asn at position 5 is modified to Asn(Trt),
      which is is trytyl-asparagine
<220> FEATURE:
<221> NAME/KEY: misc_feature
<222> LOCATION: (9)..(9)
<223> OTHER INFORMATION: Tyr at position 9 is modified to Tyr(tBu),
      which is tert-butyl-tyrosine
<220> FEATURE:
<221> NAME/KEY: misc_feature
<222> LOCATION: (10)..(10)
<223> OTHER INFORMATION: Cys at position 10 is modified to Cys(Trt),
      which is trytyl-cysteine, and Cys(Trt) is connected to a resin

<400> SEQUENCE: 6

Xaa Leu Tyr Glu Asn Val Gly Met Tyr Cys
1               5                   10
```

```
<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Gla, which is gamma-carboxy-L-glutamic
      acid
<220> FEATURE:
<221> NAME/KEY: misc_feature
<222> LOCATION: (1)..(1)
<223> OTHER INFORMATION: Xaa has a ClCH2C(O)- group attached
<220> FEATURE:
<221> NAME/KEY: misc_feature
<222> LOCATION: (9)..(9)
<223> OTHER INFORMATION: Tyr at position 9 has a -C(CH2SH)C(O)NH2 group
      attached

<400> SEQUENCE: 7

Xaa Leu Tyr Glu Asn Val Gly Met Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Adi, which is alpha-amino-adipic acid
<220> FEATURE:
<221> NAME/KEY: misc_feature
<222> LOCATION: (1)..(1)
<223> OTHER INFORMATION: Xaa has a CH2CO- group attached
<220> FEATURE:
<221> NAME/KEY: misc_feature
<222> LOCATION: (1)..(10)
<223> OTHER INFORMATION: Xaa (Adi) and Cys are bridged together, making
      this peptide cyclic
<220> FEATURE:
<221> NAME/KEY: misc_feature
<222> LOCATION: (10)..(10)
<223> OTHER INFORMATION: Cys is an amide, i.e., C(O)NH

<400> SEQUENCE: 8

Xaa Leu Tyr Glu Asn Val Gly Met Tyr Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: At position 1, Xaa = Adi, which is alpha-amino-
      adipic acid
<220> FEATURE:
<221> NAME/KEY: misc_feature
<222> LOCATION: (1)..(10)
<223> OTHER INFORMATION: Xaa (Adi) at position 1 and Cys are bridged
      together, making this peptide cyclic
<220> FEATURE:
<221> NAME/KEY: misc_feature
<222> LOCATION: (4)..(4)
<223> OTHER INFORMATION: At position 4, Xaa = Adi, which is alpha-amino-
      adipic acid
```

```
<220> FEATURE:
<221> NAME/KEY: misc_feature
<222> LOCATION: (10)..(10)
<223> OTHER INFORMATION: Cys is an amide, i.e., C(O)NH

<400> SEQUENCE: 9

Xaa Leu Tyr Xaa Asn Val Gly Met Tyr Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Glu has a CH2CO- group attached
<220> FEATURE:
<221> NAME/KEY: misc_feature
<222> LOCATION: (1)..(10)
<223> OTHER INFORMATION: Glu and Cys are bridged together, making this
      peptide cyclic
<220> FEATURE:
<221> NAME/KEY: misc_feature
<222> LOCATION: (8)..(8)
<223> OTHER INFORMATION: Xaa = Nle, which is norleucine

<400> SEQUENCE: 10

Glu Leu Tyr Glu Asn Val Gly Xaa Tyr Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Glu at position 1 is modified to Glu(OtBu),
      which is tert-butoxy-glutamic acid
<220> FEATURE:
<221> NAME/KEY: misc_feature
<222> LOCATION: (3)..(3)
<223> OTHER INFORMATION: Tyr at position 3 is modified to Tyr(OtBu),
      which is tert-butoxy-tyrosine
<220> FEATURE:
<221> NAME/KEY: misc_feature
<222> LOCATION: (4)..(4)
<223> OTHER INFORMATION: Glu at position 4 is modified to Glu(OtBu),
      which is tert-butoxy-glutamic acid
<220> FEATURE:
<221> NAME/KEY: misc_feature
<222> LOCATION: (5)..(5)
<223> OTHER INFORMATION: Asn at position 5 is modified to Asn(Trt),
      which is trityl-asparagine
<220> FEATURE:
<221> NAME/KEY: misc_feature
<222> LOCATION: (9)..(9)
<223> OTHER INFORMATION: Tyr at position 9 is modified to Tyr(OtBu),
      which is tert-butoxy-tyrosine
<220> FEATURE:
<221> NAME/KEY: misc_feature
<222> LOCATION: (10)..(10)
<223> OTHER INFORMATION: Xaa = Nle, which is norleucine
<220> FEATURE:
<221> NAME/KEY: misc_feature
<222> LOCATION: (10)..(10)
<223> OTHER INFORMATION: Xaa is an amide and is attached to a resin

<400> SEQUENCE: 11
```

```
Glu Leu Tyr Glu Asn Val Gly Met Tyr Xaa
1               5                   10
```

<210> SEQ ID NO 12
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Glu at position 1 and Cys are bridged together,
      making this peptide cyclic
<220> FEATURE:
<221> NAME/KEY: misc_feature
<222> LOCATION: (8)..(8)
<223> OTHER INFORMATION: Xaa = Nle, which is norleucine
<220> FEATURE:
<221> NAME/KEY: misc_feature
<222> LOCATION: (10)..(10)
<223> OTHER INFORMATION: Cys is an amide, i.e., C(O)NH

<400> SEQUENCE: 12

```
Glu Leu Tyr Glu Asn Val Gly Xaa Tyr Cys
1               5                   10
```

<210> SEQ ID NO 13
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Glu at position 1 and Xaa (Adi) are bridged
      together, making this peptide cyclic
<220> FEATURE:
<221> NAME/KEY: misc_feature
<222> LOCATION: (8)..(8)
<223> OTHER INFORMATION: Xaa at position 8 is Nle, which is norleucine
<220> FEATURE:
<221> NAME/KEY: misc_feature
<222> LOCATION: (10)..(10)
<223> OTHER INFORMATION: Xaa at position 10 is Adi, which is alpha-
      amino-adipic acid
<220> FEATURE:
<221> NAME/KEY: misc_feature
<222> LOCATION: (10)..(10)
<223> OTHER INFORMATION: Xaa (Adi) is an amide, i.e., C(O)NH2

<400> SEQUENCE: 13

```
Glu Leu Tyr Glu Asn Val Gly Xaa Tyr Xaa
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Glu at position 1 is modified to Glu(OtBu),
      which is tert-butoxy-glutamic acid
<220> FEATURE:
<221> NAME/KEY: misc_feature
<222> LOCATION: (4)..(4)
<223> OTHER INFORMATION: Glu at position 4 is modified to Glu(OtBu),
      which is tert-butoxy-glutamic acid
<220> FEATURE:
<221> NAME/KEY: misc_feature

```
<222> LOCATION: (5)..(5)
<223> OTHER INFORMATION: Asn at position 5 is modified to Asn(Trt),
      which is trytyl-asparagine
<220> FEATURE:
<221> NAME/KEY: misc_feature
<222> LOCATION: (9)..(9)
<223> OTHER INFORMATION: Tyr at position 9 is modified to Tyr(OtBu),
      which is tert-butoxy-tyrosine
<220> FEATURE:
<221> NAME/KEY: misc_feature
<222> LOCATION: (10)..(10)
<223> OTHER INFORMATION: Xaa = Adi(OAl), which is allyloxy-alpha-amino-
      adipic acid
<220> FEATURE:
<221> NAME/KEY: misc_feature
<222> LOCATION: (10)..(10)
<223> OTHER INFORMATION: Xaa is an amide, i.e., C(O)NH

<400> SEQUENCE: 14

Glu Leu Tyr Glu Asn Val Gly Met Tyr Xaa
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Tyr at position 4 is modified to pTyr, which is
      phosphotyrosine

<400> SEQUENCE: 15

Lys Pro Phe Tyr Val Asn Val
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Tyr at position 2 is modified to pTyr, which is
      phosphotyrosine

<400> SEQUENCE: 16

Phe Tyr Val Asn Val
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Leu Tyr Glu Asn Val
1               5

<210> SEQ ID NO 18
<211> LENGTH: 26
<212> TYPE: PRT
<213> ORGANISM: Artificial Sequence
<220> FEATURE:
<223> OTHER INFORMATION: Synthetic
```

```
-continued

<220> FEATURE:
<221> NAME/KEY: misc_feature
<222> LOCATION: (1)..(1)
<223> OTHER INFORMATION: Xaa = Gla, which is gamma-carboxy-L-glutamic
      acid

<400> SEQUENCE: 18

Xaa Leu Tyr Glu Asn Val Gly Met Tyr Cys Ala Ala Val Ala Leu Leu
1               5                   10                  15

Pro Ala Val Leu Leu Ala Leu Leu Ala Pro
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Gla, which is gamma-carboxy-L-glutamic
      acid
<220> FEATURE:
<221> NAME/KEY: misc_feature
<222> LOCATION: (1)..(1)
<223> OTHER INFORMATION: Xaa (Gla) has a CH2CO- group attached
<220> FEATURE:
<221> NAME/KEY: misc_feature
<222> LOCATION: (10)..(10)
<223> OTHER INFORMATION: Cys is an amide, i.e., C(O)NH

<400> SEQUENCE: 19

Xaa Leu Tyr Glu Asn Val Gly Met Tyr Cys Ala Ala Val Ala Leu Leu
1               5                   10                  15

Pro Ala Val Leu Leu Ala Leu Leu Ala Pro
            20                  25
```

What is claimed is:

1. A compound of formula:

[SEQ ID NO:2]

$$HN\text{-}aa^1\text{-}Leu^2\text{-}Tyr^3\text{-}aa^4\text{-}Asn^5\text{-}Val^6\text{-}Gly^7\text{-}Met^8\text{-}Tyr^9\text{-}NH$$
$$|\qquad\qquad\qquad\qquad\qquad\qquad\qquad\qquad|$$
$$C(O)\text{--------}CH_2\text{-------}L\text{--------}CH_2\text{-----}CHC(O)NH_2,$$

in which L is sulfur, sulfoxide, oxygen or methylene, in which (i) $aa^1$ is L-α-amino-adipic acid (Adi) and $aa^4$ is Glu or (ii) each of $aa^1$ and $aa^4$ is Adi, in which, optionally, one or more of $Tyr^3$, $Val^6$, $Met^8$ and $Tyr^9$ is substituted with a D-configuration analog thereof or $Met^8$ is substituted with $Nle^8$, and in which, optionally, there is a conservative or neutral amino acid substitution at either one or both of $Leu^2$ and $Gly^7$, wherein said compound binds an SH2 domain in a protein comprising an SH2 domain, is non-phosphorylated, and whereupon binding to a growth factor receptor-bound protein 2 (Grb2), the compound has a turn conformation.

2. A conjugate comprising a compound of claim 1 and a carrier agent.

3. The conjugate of claim 2, wherein said carrier agent is a signal peptide, antennapedia peptide, or lipofectin.

4. A composition comprising a compound of claim 1 and a carrier.

5. A composition comprising a conjugate of claim 2 and a carrier.

6. A method of synthesizing a conjugate comprising (i) compound of formula:

[SEQ ID NO:2]

$$HN\text{-}aa^1\text{-}Leu^2\text{-}Tyr^3\text{-}aa^4\text{-}Asn^5\text{-}Val^6\text{-}Gly^7\text{-}Met^8\text{-}Tyr^9\text{-}NH$$
$$|\qquad\qquad\qquad\qquad\qquad\qquad\qquad\qquad|$$
$$C(O)\text{--------}CH_2\text{-------}L\text{--------}CH_2\text{-----}CHC(O)NH_2,$$

in which L is sulfur, sulfoxide, oxygen or methylene, in which (i) $aa^1$ is L-α-amino-adipic acid (Adi) and $aa^4$ is Glu or (ii) each of $aa^1$ and $aa^4$ is Adi, in which, optionally, one or more of $Tyr^3$, $Val^6$, $Met^8$ and $Tyr^9$ is substituted with a D-configuration analog thereof or $Met^8$ is substituted with $Nle^8$, and in which, optionally, there is a conservative or neutral amino acid substitution at either one or both of $Leu^2$ and $Gly^7$, wherein said compound binds an SH2 domain in a protein comprising an SH2 domain, is non-phosphorylated, and whereupon binding to a growth factor receptor-bound protein 2 (Grb2), the compound has a turn conformation, and (ii) a carrier agent, which comprises:

(a) synthesizing from C-terminus to N-terminus a linear side-chain protected peptide comprising from N-terminus to C-terminus the amino acid sequence of the compound and the amino acid sequence of a carrier agent on an amide resin, (b) N-terminally haloacetylating the peptide, (c) cleaving the peptide from the resin and, either simultaneously or sequentially, deprotecting the side-chains of the peptide, (d) nucleophilically displacing the N-terminal halo group with the cysteine side-chain thiol functionality at from about pH 7 to about pH 8, and (e) purifying the resulting conjugate.

7. The method of claim 6, wherein haloacetylating is bromoacetylating or chloroacetylating.

* * * * *